(12) United States Patent
Hidaka et al.

(10) Patent No.: US 6,319,515 B1
(45) Date of Patent: Nov. 20, 2001

(54) ISOSORBIDE DINITRATE-CONTAINING PATCH

(75) Inventors: Osafumi Hidaka; Satoshi Murakami; Yoshifusa Tachimori; Michisuke Ohe, all of Hamura (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/142,492

(22) PCT Filed: Jan. 6, 1998

(86) PCT No.: PCT/JP98/00009

§ 371 Date: Sep. 8, 1998

§ 102(e) Date: Sep. 8, 1998

(87) PCT Pub. No.: WO98/30210

PCT Pub. Date: Jul. 16, 1998

(30) Foreign Application Priority Data

Jan. 7, 1997 (JP) .......................................................... 9-651
Sep. 26, 1997 (JP) ................................................... 9-261645

(51) Int. Cl.$^7$ .................................................... A61F 13/00
(52) U.S. Cl. .......................... 424/449; 424/448; 514/465; 514/947; 602/52; 604/307
(58) Field of Search .................................... 424/448, 449; 514/465, 947; 602/52; 604/307

(56) References Cited

FOREIGN PATENT DOCUMENTS

| | | |
|---|---|---|
| 0223524 | 5/1987 | (EP) . |
| 0379045 | 7/1990 | (EP) . |
| 0 435 199 A2 | 7/1991 | (EP) . |
| 57-116011 | 8/1982 | (JP) . |
| 32-23212 | 7/1991 | (JP) . |
| 6329539 A | 11/1994 | (JP) . |
| 6345640 | 12/1994 | (JP) . |
| WO 95/22970 | 8/1995 | (WO) . |

Primary Examiner—Jose' G. Dees
Assistant Examiner—Michael A. Williamson
(74) Attorney, Agent, or Firm—Sughrue, Mion, Zinn, Macpeak & Seas, PLLC

(57) ABSTRACT

The present invention relates to an isosorbide dinitrate-containing patch, in which an adhesive layer comprising an adhesive composition is formed on a flexible support, and the adhesive composition consists of an acrylic-based adhesive (A), a polyvinyl acetate-based adhesive (B), a plasticizing component (C) and isosorbide dinitrate (D), and satisfies the following weight ratios (1) through (3) of each of the components:

(1) A:B=70:30 to 10:90,
(2) the weight ratio of the component C based on the adhesive composition is 10 to 40% by weight, and
(3) the weight ratio of the component D based on the adhesive composition is 20 to 35% by weight.

Provided is a patch excellent in percutaneous absorption, handleability, resistance to skin irritation, sustained release, adhesivity, etc.

26 Claims, 1 Drawing Sheet

ISOSORBIDE DINITRATE-CONTAINING PATCH

TECHNICAL FIELD

The present invention relates to an isosorbide dinitrate-containing patch. More specifically, the present invention relates to a patch, for example, having advantageous points such as excellent sustained release and good percutaneous absorption, in which an adhesive layer comprising an adhesive composition is formed on a flexible support, and the adhesive composition consists of an acrylic-based adhesive, a polyvinyl acetate-based adhesive, a plasticizing active component and isosorbide dinitrate at specific weight ratios.

BACKGROUND ART

Isosorbide dinitrate-containing patches are commonly known, and it is indicated, for example, in Japanese Unexamined Patent Publication No. 57-116011, etc., that pressure-sensitive adhesives such as silicone-based, rubber-based or acrylic-based adhesives are preferable as pressure-sensitive adhesives used in these patches. In addition, at the 5th meeting of the Japan Pharmacology Association (Sep. 26–28, 1989), Oguche, et al. reported that with respect to patches containing isosorbide dinitrate, they compared acrylic-based, silicone-based and rubber-based adhesives with each other and found the percutaneous absorption of these three are roughly equal.

The above-mentioned Japanese Unexamined Patent Publication No. 57-116011 was later published after examination (Japanese Examined Patent Publication No. 4-74329) with an amendment stating that acrylic-based pressure-sensitive adhesives are particularly preferable among various types of pressure-sensitive adhesives.

Namely, in conventional isosorbide dinitrate-containing patches, with respect to the relationship between the percutaneous absorption of isosorbide dinitrate and the pressure-sensitive adhesive, it was considered that acrylic-based adhesives are preferable, or that the above-mentioned acrylic-based adhesives and rubber-based adhesives are equally preferable.

One of the shortcomings of patches is the occurrence of rashes on the skin, and various proposals have been made as methods to suppress it. One method involves reducing the size of the preparation so that the portion of the skin where the rash occurs will be smaller. However, it is necessary to increase the amount of percutaneous absorption per unit area in order to accomplish this. Although various types of absorption promoters were proposed for adding to a patch (an adhesive layer) in order to increase the amount of percutaneous absorption, due in part to the fact that absorption promoters generally have a low molecular weight, they often demonstrate skin irritation. In addition, there are also problems including a decrease in the adhesive strength of the resultant adhesive composition when large amounts of absorption promoters are added. Thus, a patch that suppresses the occurrence of skin rash while also offering excellent percutaneous absorption and adhesive strength has not been successfully provided yet.

For example, for the purpose of providing an isosorbide dinitrate-containing patch good in balance between adhesivity and skin irritation, a patch prepared by adding isopropyl myristate in a large amount as a plasticizing component to an acrylic-based adhesive has been proposed (Japanese Unexamined Patent Publication No. 3-223212). However, since an acrylic-based adhesive is not sufficiently good in compatibility with isosorbide dinitrate, isosorbide dinitrate as crystals in an adhesive layer when the concentration of isosorbide dinitrate is higher than about 10–15% by weight. Even in the case of such a high content of isosorbide dinitrate, therefore it is considered that the promotion effect in percutaneous absorption is little, and the main effect is only the extension of releasing time.

In order to increase absorbability, it is desirable to use an adhesive composition capable of dissolving isosorbide dinitrate in high concentration, and it has been discovered that polyvinyl acetate-based adhesives are preferable as such adhesive composition (Japanese Unexamined Patent Publication No. 6-329539, Japanese Unexamined Patent Publication No. 6-345640 and International Publication No. WO95-22970).

Such polyvinyl acetate-based adhesives have demonstrated superior promotion effect on percutaneous absorption to conventional pressure-sensitive adhesives. However, when an isosorbide dinitrate-containing patch is compared with a glycerol nitrate-containing patch, in which both the active ingredients are typical percutaneous coronary vasodilators, a minimum-sized isosorbide dinitrate-containing patch on market is 30 $cm^2$ while a minimum-sized glycerol nitrate-containing patch on market is 20 $cm^2$. Namely, for increasing the percutaneous absorption of isosorbide dinitrate from an isosorbide dinitrate-containing patch in such a degree that the compliance of a patient is improved, further improvement in percutaneous absorption is required. This improvement enables the downsizing of patches so that skin irritation is reduced.

Namely, one of the objects of the present invention is to provide an isosorbide dinitrate-containing patch little in skin irritation and excellent in percutaneous absorption.

Another object of the present invention is to provide an isosorbide dinitrate-containing patch little in skin irritation, excellent in percutaneous absorption and having sustained release.

Further another object of the present invention is to provide an isosorbide dinitrate-containing patch having an adequate degree of adhesive strength and hardly giving pain on the removal of an applied patch.

Still another object of the present invention is to provide an isosorbide dinitrate-containing patch resistant to peeling and stably attached on the skin in use in spite that it has no strong adhesive strength.

Yet another object of the present invention is to provide an isosorbide dinitrate-containing patch which is contrived so as to exhibit excellent handleability even for elderly persons, whose ratio in the patients is high.

The inventors of the present invention have zealously pursued studies for achieving the above-mentioned tasks and completed the present invention by finding that the combination of an acrylic-based adhesive (A), a polyvinyl acetate-based adhesive (B), a plasticizing component (C) and isosorbide dinitrate (D) at specific ratios by weight can attain the objects of the present invention, which can not be achieved by conventional techniques.

DISCLOSURE OF THE INVENTION

The present invention relates to a patch in which an adhesive layer comprising an adhesive composition is formed on a flexible support and more specifically, relates to an isosorbide dinitrate-containing patch in which the adhesive composition comprises an acrylic-based adhesive (A), a polyvinyl acetate-based adhesive (B), a plasticizing component (C) and isosorbide dinitrate (D), and the following weight ratios (1) through (3) of each of the components are satisfied at the same time:

(1) A:B=70:30 to 10:90, (2) the weight ratio of the component C based on the adhesive composition is 10 to 40% by weight, and (3) the weight ratio of the component D based on the adhesive composition is 20 to 35% by weight, and the present invention also provides a method for producing the patch.

BEST MODE FOR CARRYING OUT THE INVENTION

Figure 1:
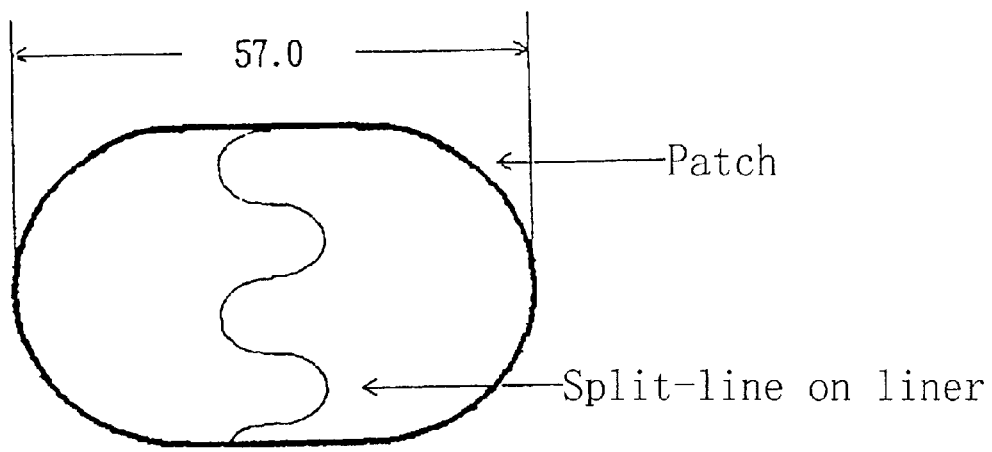
FIG. 1 is a reference drawing showing an ordinary patch prepared in Example 12, and the patch has a major axis of 57 mm and a split-line on liner.

Preferable examples of the acrylic-based adhesive (A) of the present invention include a pressure-sensitive adhesive prepared by copolymerizing a (meth)acrylic acid alkyl ester whose alkyl group has a mean carbon number of 3 to 14 in an amount of at least 25% or more by weight. In view point that a patch has little skin irritation, an adequate degree of stickiness and adhesion, a high degree of internal cohesion and excellent solvent resistance, in particular, (1) preferable is an acrylic-based adhesive prepared by copolymerizing a (meth)acrylic acid alkyl ester whose alkyl group has a mean carbon number of 4 or more, preferably 4 to 14 in an amount of at least 50% or more, preferably 50 to 98% by weight, and (2) particularly preferable is an acrylic-based adhesive prepared by copolymerizing a (meth)acrylic acid alkyl ester whose alkyl group has a mean carbon number of 4 or more, preferably 4 to 14 in an amount of at least 50% or more, preferably 50 to 98% by weight and acrylic acid and/or methacrylic acid in an amount of 2–50% by weight.

Examples of the (meth)acrylic acid alkyl ester whose alkyl group has a mean carbon number of 3–14 include butyl (meth)acrylate, amyl (meth)acrylate, hexyl (meth)acrylate, heptyl (meth)acrylate, octyl (meth)acrylate, nonyl (meth)acrylate, decyl (meth)acrylate, 2-ethylhexyl (meth)acrylate, etc.

As the acrylic-based adhesive (A) of the present invention, one or more kinds of the above-mentioned examples of acrylic-based adhesive can be used as a mixture. Further, the acrylic-based adhesive of the present invention optionally contains a known organic or inorganic crosslinking agent in an amount of 0.01–10% by weight.

Preferable examples of the polyvinyl acetate-based adhesive (B) of the present invention include a pressure-sensitive adhesive having a copolymerization ratio of vinyl acetate of at least 50% or more by weight. Such pressure-sensitive adhesive may be, for example, a copolymer of vinyl acetate, and a (meth)acrylic acid alkyl ester and/or (meth)acrylic acid, a copolymer of vinyl acetate and a vinyl ether such as vinyl butyl ether, etc.

Herein, as the acrylic acid alkyl ester, for example, a (meth)acrylic acid alkyl ester whose alkyl group has a mean carbon number of 3 to 14 is preferable. Examples of the (meth)acrylic acid alkyl ester may be same as those exemplified in the above-mentioned acrylic-based adhesive (A).

As the polyvinyl acetate-based adhesive (B) of the present invention, a polyvinyl acetate-based adhesive composed of a copolymer of vinyl acetate, and a (meth)acrylic acid alkyl ester and/or (meth)acrylic acid is preferable among the above-mentioned copolymers, and a copolymer of vinyl acetate, and a (meth)acrylic acid alkyl ester whose alkyl group has a mean carbon number of 3 to- 14 and/or (meth)acrylic acid is particularly preferable among these substances. In particular, a copolymer of vinyl acetate, a (meth)acrylic acid alkyl ester whose alkyl group has a mean carbon number of 3 to 14 and (meth)acrylic acid, concretely a copolymer of vinyl acetate, 2-ethylhexyl (meth)acrylate and (meth)acrylic acid is preferable.

In cases where the polyvinyl acetate-based adhesive (B) of the present invention is a copolymer of vinyl acetate, and a (meth)acrylic acid alkyl ester whose mean carbon number of the alkyl group is 3 to 14 and/or (meth)acrylic acid, the copolymerization ratio of vinyl acetate:(meth)acrylic acid ester and/or acrylic acid is preferably 50:50 to 90:10, particularly preferably 60:40 to 80:20, further particularly preferably 70:30. In particular, a copolymer having the copolymerization ratios of vinyl acetate:(meth)acrylic acid alkyl ester (particularly, 2-ethylhexyl (meth)acrylate):(meth) acrylic acid of 70:27.5:2.5 can be cited as a preferable example. Further, in the copolymer of vinyl acetate, and a (meth)acrylic acid alkyl ester and/or (meth)acrylic acid, the copolymerization ratio of (meth)acrylic acid is preferably 0–10%, particularly preferably 1–5% by weight.

Regarding the molecular weight of the polyvinyl acetate-based adhesive (B), a weight average molecular weight (Mw) is preferably 150,000 to 1,000,000 when expressed in terms of polystyrene. A polyvinyl acetate-based adhesive having a molecular weight of less than 150,000 is not satisfactory since it has a trouble of flowing and a part of the adhesive remains on the skin when the patch is removed after application on the skin, causing so called "remaining adhesive". On the other hand, a polyvinyl acetate-based adhesive having a molecular weight of more than 1,000,000 tends to be insufficient in adhesive strength. A polyvinyl acetate-based adhesive having a molecular weight of 200,000 to 1,000,000 can be cited as a preferable one. Herein, a number average molecular weight (Mn) should be in an ordinary range, that is, Mw (weight average molecular weight)/Mn is in the range of 3 to 10, preferably in the range of 4 to 8.

The plasticizing component (C) of the present invention may be selected from the group comprising, for example, a saturated and an unsaturated acids whose carbon numbers are 12 or more such as myristic acid, oleic acid, palmitic acid and lauric acid, their esters such as isopropyl myristate, ethyl oleate, isopropyl palmitate, octyl palmitate and ethyl laurate, and triethyl citrate, isopropyl adipate, triacetin, etc. Among these plasticizing components (C), an ester of a saturated or unsaturated fatty acid having a carbon number of 12 to 20 is preferable, and isopropyl myristate and ethyl oleate are particularly preferable since they have good compatibility with the polyvinyl acetate-based adhesive (B) and the acrylic-based adhesive (A).

Examples of a preferable combination of the acrylic-based adhesive (A), the polyvinyl acetate-based adhesive (B) and the plasticizing agent (C), which constitute the adhesive composition of the adhesive layer of the present invention, include (1) a combination of an acrylic-based adhesive (A) obtained by copolymerizing at least 25% or more (meth)acrylic acid alkyl ester by weight whose alkyl group has a mean carbon number of 3 to 14, a polyvinyl acetate-based adhesive (B) having a vinyl acetate-copolymerization ratio of 50% or more by weight and a plasticizing agent (C) of a saturated or unsaturated fatty acid whose carbon number is 12 or more or its ester, particularly (2) a combination of an acrylic-based adhesive (A) obtained by copolymerizing at least 50 to 98% (meth)acrylic acid alkyl ester by weight whose alkyl group has a mean carbon number of 4 to 14, a polyvinyl acetate-based adhesive (B) obtained by copolymerizing vinyl acetate, and a (meth)acrylic acid alkyl ester and/or (meth)acrylic acid in which the copolymerization ratio of the vinyl acetate is at least 50% or more by weight and a plasticizing agent (C) comprising an ester of a saturated or unsaturated fatty acid whose carbon number is 12 to 20, particularly preferably (3) a combination of an acrylic-based adhesive (A) obtained by copolymerizing 50 to 98% (meth)acrylic acid alkyl ester by weight whose alkyl group has a mean carbon number of 4 to 14 and 2–50% acrylic acid and/or methacrylic acid by weight, a polyvinyl acetate-based adhesive (B) obtained by copolymerizing vinyl acetate, and a (meth)acrylic acid alkyl ester whose alkyl group has a mean carbon number of 3 to 14 and/or (meth)acrylic acid, especially vinyl acetate, a (meth)acrylic acid alkyl ester whose alkyl group has a mean carbon number of 3 to 14 and (meth)acrylic acid in which the copolymerization ratio of the vinyl acetate is at least 50% by weight and a plasticizing agent (C) comprising isopropyl myristate or ethyl oleate, and still particularly preferably (4) a combination of an acrylic-based adhesive (A) obtained by copolymerizing 90% 2-ethylhexyl (meth)acrylate and 10% (meth)acrylic acid by weight, a polyvinyl acetate-based adhesive (B) obtained by copolymerizing vinyl acetate, 2-ethylhexyl (meth)acrylate and (meth)acrylic acid, particularly in which copolymerization ratios of vinyl acetate: (meth)acrylic acid alkyl ester (particularly, 2-ethylhexyl (meth)acrylate):(meth)acrylic acid are 70:27.5:2.5, and a plasticizing agent (C) comprising isopropyl myristate or ethyl oleate.

Further, in the above-mentioned preferable combinations, in cases where the polyvinyl acetate-based adhesive (B) is the copolymer of vinyl acetate, and a (meth)acrylic acid alkyl ester whose alkyl group has a mean carbon number of 3 to 14 and/or (meth)acrylic acid, the copolymerization ratio of vinyl acetate : (meth)acrylic acid alkyl ester and/or acrylic acid is preferably 50:50 to 90:10, particularly 60:40 to 80:20, further particularly 70:30. Furthermore, in the copolymer of vinyl acetate, and a (meth)acrylic acid alkyl ester and/or (meth)acrylic acid, the copolymerization ratio of (meth)acrylic acid is preferably 0 to 10%, particularly 1 to 5% by weight.

The adhesive composition of the present invention is mainly composed of such acrylic-based adhesive (A), polyvinyl acetate-based adhesive (B), plasticizing component (C) and isosorbide dinitrate (D), and the weight ratios of each component satisfy the following (1) through (3):

(1) A:B=70:30 to 10:90,
(2) the weight ratio of C based on the adhesive composition is 10 to 40% by weight, and
(3) the weight ratio of D based on the adhesive composition is 20 to 35% by weight.

These specific weight ratios enable the achievement of the above-mentioned objects of the present invention, for example, the enhancement of percutaneous absorption promotion effect and the optimization of adhesive strength into a preferable region for a patch.

Particularly preferable weight ratios of components in points of percutaneous absorption promotion effect, adhesive strength, etc., satisfy the following (1) through (3):

(1) A:B=50:50 to 10:90,
(2) the weight ratio of C based on the adhesive composition is 20 to 40% by weight, and
(3) the weight ratio of D based on the adhesive composition is 20 to 35% by weight.

In the present invention, the use of the acrylic-based adhesive (A) and the polyvinyl acetate-based adhesive (B) at a ratio of A:B=70:30 to 10:90 is preferable for achieving the objects of the present invention such as an effect on percutaneous absorption, and a ratio of A:B=50:50 to 10:90 is particularly preferable since it achieves particularly good results in points of percutaneous absorption promotion effect and adhesive strength.

The higher the weight ratio of the plasticizing component (C) in the adhesive composition in the range of 10 to 40% by weight was, the further excellent the percutaneous absorption became. On the other hand, it became clear that when the weight ratio exceeded 40%, internal adhesive strength of the pressure-sensitive adhesive largely decreased and it caused troubles such as "remaining adhesive" when the patch was applied on human body, etc.

Further, the higher the weight ratio of the isosorbide dinitrate (D) in the adhesive composition in the range of 20 to 35% by weight, the higher the percutaneous absorption gradually became. However, when it was 30% or more by weight, the percutaneous absorption showed a tendency to become a little smaller, and when it exceeded 35% by weight, the percutaneous absorption decreased contrarily-and the adhesive strength decreased extremely.

Generally, it is supposed that when higher weight ratios of the plasticizing component (C) and also of the isosorbide dinitrate (D) based on the adhesive layer are adopted, the percutaneous absorption will increase. However, when weight ratios of the plasticizing component (C) and the isosorbide dinitrate (D) are made too high, an adhesive strength, which is another important characteristic in a patch and an indispensable function for a patient to safely keep the patch applied on the skin, will decrease and the frequency of the phenomena of "remaining adhesive" is apt to become large.

Differently, in the present invention, even in cases where the weight ratios of the plasticizing component (C) and the isosorbide dinitrate (D) are increased in such a manner as mentioned above, the objects of the present invention, for example, such as the improvement of percutaneous absorption and the keeping of an adequate degree of the adhesive strength can be attained.

Regarding the mechanism of the effect of the present invention, the inventors estimate that the polyvinyl acetate-based adhesive (B) has a role for keeping the isosorbide dinitrate at high concentration without crystallizing it, the acrylic-based adhesive (A) has a role for making the isosorbide dinitrate easy to diffuse, and existing in spaces of entanglement among the acrylic-based adhesive (A) molecules and the polyvinyl acetate-based adhesive (B) molecules, the plasticizing component (C) helps the diffusion of the isosorbide dinitrate molecules.

That is, when the plasticizing component (C) and the isosorbide dinitrate (D) were added into the pressure-sensitive adhesive consisting only of the polyvinyl acetate-based adhesive (B) even in the preferable ranges of the present invention, the patch prepared by using the resultant adhesive composition could not give sufficient percutaneous absorption. Further, the patch was not sufficient in the adhesive strength, which is an important factor as patch.

Furthermore, when the plasticizing component (C) and the isosorbide dinitrate (D) were added into the pressure-sensitive adhesive consisting only of the acrylic-based adhesive (A) even in the preferable ranges of the present invention, the patch prepared by using the resultant adhesive composition had the percutaneous absorption in a low level. In the case of the single use of the acrylic-based adhesive (A), comparing with the patch prepared without using the plasticizing component (C), the patch prepared by using the plasticizing component (C) demonstrated a higher level of percutaneous absorption. However, the level of percutaneous absorption of this patch was far low from the objective level in the present invention.

The adhesive layer of the present invention can be prepared by simultaneously mixing the above-mentioned components (A) through (D) in the preferable combination and weight ratios as described above, by preparing an adhesive composition substantially free from the component D in advance and subsequently allowing the adhesive layer composed of this adhesive composition to contain the component D as shown below, or by mixing these components according to other known methods.

Generally, the thickness of such adhesive layer may be adjusted to a level which is common as thickness of the adhesive layer of a patch. However, it is preferable to use a thickness of 50–120 µm, particularly preferably 60–100 µm, unless otherwise specified later in the preferred embodiment of the present invention.

In addition, the inventors studied on the possibility of obtaining a further preferable preparation using these components in a more sophisticated manner. Resultingly, the adhesive layer of the present invention is divided into (1) an adhesive composition-containing layer in which the adhesive strength is almost neglected, the isosorbide dinitrate is held in high dose, and serious consideration is put on the diffusion and absorption of the isosorbide dinitrate (designated as a reservoir layer) and (2) an adhesive composition-containing layer in which main consideration is put on the adhesive strength, and at the same time sufficient consideration is put on the abilities to release and transfer the isosorbide dinitrate to the skin (designated an adhering releasing layer); in other word, the adhesive layer of the present invention is used as the reservoir layer, and the adhering releasing layer is additionally placed. After various studies on the optimization of these layers, they completed a more preferable embodiment of the present invention.

Namely, the inventors found that in cases where the adhesive layer is composed of two or three layers composed of the acrylic-based adhesive (A), the polyvinyl acetate-based adhesive (B), the plasticizing component (C) and the isosorbide dinitrate (D), when the adhesive composition of one layer (a reservoir layer) satisfies the following conditions at the same time:
(1) A:B=60:40 to 10:90,
(2) the weight ratio of C based on the reservoir layer is 20 to 40%,
(3) the weight ratio of D based on the reservoir layer is 25 to 35%, and
(4) the thickness of the reservoir layer is 10 to 100 µm, and when the adhesive composition in the layer (an adhering releasing layer) arranged at the patient's skin side of the patch satisfies the following (1) through (4):
(1) A:B=0:100 to 100:0,
(2) the weight ratio of C based on the adhering releasing layer is 0 to 40%,
(3) the weight ratio of D based on the adhering releasing layer is 10 to 30%, and
(4) the thickness of the adhering releasing layer is 3 to 25 µm, the isosorbide dinitrate-containing patch of the present invention prepared by placing the reservoir layer and the adhering releasing layer as the adhesive layer on a flexible support can release the isosorbide dinitrate at the greatest degree while holding the isosorbide dinitrate in high dose and demonstrate excellent adhesivity to the skin.

When the adhesive layer is composed of the reservoir layer and the adhering releasing layer, as for the state of the isosorbide dinitrate in each of the reservoir layer and the adhering releasing layer, the reservoir layer contains the isosorbide dinitrate in a state where it partly precipitates as crystals, and the adhering releasing layer contains the isosorbide dinitrate in a state where it partly precipitates as crystals or the adhering releasing layer is free from crystalline isosorbide dinitrate, and the latter case is preferable since the patch of this state tends to have higher adhesive strength. In particular, for storing a patch of the present invention for a long time in a stable state, it is preferable that the isosorbide dinitrate exists in higher concentration in the reservoir layer than in the adhering releasing layer. Further, in this case, it is preferable that the isosorbide dinitrate is partly crystallized in the reservoir layer, and there is no crystal or only a small amount of crystal exists in the adhering releasing layer.

The composition of a further preferable reservoir layer satisfies the following (1) through (3):
(1) A:B=60:40 to 10:90,
(2) the weight ratio of C based on the reservoir layer is 25 to 40%, and
(3) the weight ratio of D based on the reservoir layer is 28 to 35%.

The thickness of the reservoir layer is 10 to 100 µm, preferably 30 to 80 µm, further preferably 40 to 70 µm. On the other hand, the thickness of the adhering releasing layer is 3 to 25 µm, preferably 7 to 20 µm, further preferably 5 to 15 µm. When the thickness is less than 3 µm, a sufficient adhesive strength can not be expected, and when it exceeds 25 µm, the releasability is apt to decrease.

In a particularly preferable patch, the composition of the reservoir layer satisfies the following (1) through (4):
(1) A:B=60:40 to 10:90,
(2) the weight ratio of C based on the reservoir layer is 30 to 40%,
(3) the weight ratio of D based on the reservoir layer is 28 to 35%, and
(4) the thickness of the adhesive layer of the reservoir layer is 30 to 80 µm,
the composition of the adhering releasing layer satisfies the following (1) through (4):
(1) A:B=60:40 to 10:90,
(2) the weight ratio of C based on the adhering releasing layer is 30 to 40%,
(3) the weight ratio of D based on the adhering releasing layer is 10 to 30%, and
(4) the thickness of the adhesive layer of the adhering releasing layer is 7 to 20 µm,
and further satisfies that the concentration of the isosorbide dinitrate is higher in the reservoir layer than in the adhering releasing layer, and at least a part of isosorbide dinitrate in the reservoir layer deposits as crystals.

In the present invention, the plasticizing component (C) and the isosorbide dinitrate (D) are compounded in high concentrations in the adhesive composition, and accordingly in order to heighten inner cohesion of the adhesive composition, it is preferable to use a known crosslinking agent, which can crosslink molecules in the pressure-sensitive adhesive with each other by utilizing the properties of carboxylic groups existing in molecules of the acrylic-based adhesive (A) and the polyvinyl acetate-based adhesive (B), or by other means.

Examples of the application of the crosslinking agent include: a method using polyvinylpyrrolidone in an amount of 0.005 to 2% of the adhesives (A+B); a method using aluminum acetylacetonate in an amount of 0.1 to 5% of the adhesive (A+B); a method using a compound having a di- or tri-valent metal ion in a molecule like aluminum acetylacetonate in an amount of 0.1 to 5%; and a method using a compound having a gelling activity by itself in an amount of 1 to 10% of the adhesives (A+B) by weight. In addition, applicable is a method which uses 0.1 to 5% compound (e.g. epoxide) by weight which has two or more functional groups reactive with a carboxyl group in a molecule as a crosslinking agent.

Examples of flexible materials for the support of the present invention include film, fabric such as woven fabric, knitted fabric or nonwoven fabric, and a composite material of film and fabric. The thickness of the film is preferably 0.5 to 100 $\mu$m. As materials of the film and the fabric, polyesters such as polyethylene terephthalate, polyolefins such as polyethylene or polypropylene, polyamides such as nylon 6, ethylene-vinyl acetate copolymers, etc., can be used. Among these materials, polyester is preferable in view of stability and safety.

As for the thickness of such polyester film, polyester film having a thickness in the range of 0.5 to 4.9 $\mu$m is preferable since it has sufficient strength, excellent handleability, little skin rash, good sealing property, etc. When the thickness is less than 0.5 $\mu$m, some patches prepared using the film are insufficient in strength, poor in handleability, etc., and when the thickness exceeds 4.9 $\mu$m, some patches have troubles of skin rash, poor adaptability to the skin, etc. Thereby about 1.0 to 3.5 $\mu$m in thickness is preferable in view of strength, handleability, adaptability to the skin and skin rash.

In particular, polyester film or polyethylene terephthalate film which is water-semipermeable, and has a strength of 8 to 100 g/mm in each of two directions which are substantially perpendicular to each other, an elongation of 30 to 150% in each of two directions which are substantially perpendicular to each other, the ratio of elongations in two directions of 1.0 to 4.0 (when the elongations in two directions are different from each other, the smaller one is let the denominator) and thickness of 0.5 to 4.9 $\mu$m is preferable since it can exhibit further excellent effect in strength, handleability, adaptability and skin rash.

As a fabric materials for the support of the present invention, a fabric having 5 to 60 g/m$^2$ unit area weight composed of polyester fiber, particularly a fabric having 8 to 40 g/m$^2$ unit area weight is preferable in view of skin rash and handleability. Further, a fabric having 10 to 25 g/m$^2$ unit area weight is preferable, since it is excellent in the diffusion and absorption of the isosorbide dinitrate. Herein, regarding the thickness of the fibers, there is no limitation as far as a fabric having the above-mentioned unit area weight is producible. As for the relation between the thickness of the fibers constituting a polyester hollow fiber fabric shown bellow and the unit area weight of the fabric, a fabric having a unit area weight in the above-mentioned range is preferable in the case of about 20 to 75 denier fibers composed of 0.1–5 denier single yarns. For example, about 12 to 16 g/m$^2$ unit area weight is preferable with fibers of about 20 denier; about 17 to 24 g/m$^2$ unit area weight is preferable with fibers of about 50 denier; and about 25 to 30 g/m$^2$ unit area weight is preferable with fibers of about 75 denier. Furthermore, regarding the shapes of the fabric, a woven fabric, a knitted fabric, a nonwoven fabric, etc., can be used, and particularly a knitted fabric is preferable since it has high elongation and easily fits to the skin.

In cases where above exemplified film is used as the soft materials for the support for producing a highly stable patch from which isosorbide dinitrate is hardly escape, when the film is combined with a fabric on its inside surface or outside surface through a bonding agent or a pressure sensitive adhesive to form an above-mentioned composite material of the film and the fabric with the aim of improving the handleability of the patch, the patch to be obtained using the resultant composite material, etc., will have high stability and will be excellent in handleability. Here, examples of preferable combination of a film and a fabric may include the combination of the above-mentioned polyester film or polyethylene terephthalate film which is water-semipermeable and has above-mentioned specific thickness, strength and elongation, and a fabric of polyester fibers having the above-mentioned unit area weight.

When a laminate comprising components selected from the following (a) through (e):

(a) the outermost film layer 0.5 to 100 $\mu$m thick, (b) a bonding layer 1 to 100 $\mu$m thick, (c) a fabric, (d) a bonding layer 1 to 100 $\mu$m thick, and (e) a film layer 0.5 to 100 $\mu$m thick, is used as said support of the patch of the present invention, a patch to be formed will preferably have excellent handleability. This laminate for the support may be formed by laminating each layer in-the following order from the outermost layer: (a), (b), (c), (d) and (e); (a), (c), (d) and (e); (a), (b), (c) and (e); (c), (d) and (e); or (a), (b) and (c). The components (a) and (c), and the components (c) and (e) may be directly heated and pressed to adhere them, with each other. As an agent for bonding layers (b) and (d), the pressure-sensitive adhesive of the present invention or a known acrylic-based, rubber-based or silicone-based adhesive can be used. Further, when a laminate is formed by placing layers in the order of (a), (c), (d) and (e) omitting the bonding layer (b), for example, (a) and (c) can be laminated each other by means of adhesive strength of the bonding layer (d) by selecting fabric (c) having small unit area weight.

Especially preferable support of invention among these examples is obtained when the following conditions or states are satisfied at the same time: (a) and (e) are each a polyester film 0.5 to 4.9 $\mu$m thick, especially a water-semipermeable polyester film or polyethylene terephthalate film having strengths of 8 to 100 g/mm both in two directions substantially perpendicular to each other, elongations of 30 to 150% both in two directions substantially perpendicular to each other, the ratio of the elongations between the two directions of 1.0 to 4.0 (when the elongations in both directions are different from each other, the smaller one is let the denominator) and 0.5–4.9 $\mu$m thick ; (c) is a polyester fabric having 8 to 40 g/m$^2$ unit area weight; (b) and (d) are boding layers each 5–50 $\mu$m thick; and these layers, are pressed to laminate in the order of (a), (c), (c), (d) and (e). This support will give a patch having excellent handleability and dimensional stability, and the support is preferable also in view of productivity.

In addition, as another preferable form of a patch, one can cite a patch in which the film layer (e) is placed on a pressure-sensitive adhesive layer of the present invention, and the fabric (c) is buried in the pressure-sensitive adhesive layer at the human skin layer side of the film layer (e), or the fabric or fabrics (c) are sandwiched between or among above-mentioned two or more pressure-sensitive adhesive layers, and this patch is excellent in flexibility and handleability. Further, on the removal of the solvent in the pressure-sensitive adhesive layer, a fabric layer, if it exists, provides pathways for the vapor in the pressure-sensitive adhesive layer and enables the easy removal of the residual solvent. This is especially favorable since the easiness of the removal of the residual solvent advantageously affects the improvement of safety.

Further, as another preferable mode, one can cite a case of a detachable support. In this case, when the support consists of, for example, (a), (b), (c), (d) and (e); (c), (d) and (e); or (a), (c), (d) and (e), the adhesive strength of (d) may be kept extremely weak. Also, when the support consists of (a), (b), (c) and (e), the adhesive strength of (b) may be kept extremely weak. If a patch is the latter case, an isosorbide dinitrate-containing adhesive layer and a support comprising the laminate of this series is handled as a unit, and while the patch is continuously used keeping it on the human skin, the isosorbide dinitrate-containing adhesive layer and only the film (e) as a support can be left on the human skin. That is, one can produce a support containing an easily detachable supporter using a flexible support. Such a support is preferable since a patch produced by using it gives extremely suppressed foreign feeling.

In order to extremely weaken the adhesive strengths of (d) or (b), which decide their adhesions to (e), the following method can be used. That is, for example, an acrylic-based adhesive is compounded with a liquid component such as isopropyl myristate in an amount of 20 to 50% of its solid component of the acrylic-based adhesive by weight, and additionally a two- or three-valent metal ion is added in an amount of 20 to 70% based on the number of the carboxyl groups in the solid of the acrylic-based adhesive to cross link, crosslinking is formed with a compound having a two- or more-valent functional group, and/or crosslinking effect is enhanced with a compound such as polyvinylpyrrolidone.

For enabling a patient to easily handle a patch composed of such detachable support, it is preferable to color some or all of (a), (b), (c), (d) and (e), especially the fabric (c), in view of production cost, in red, blue, flesh color, etc. Among them, the case where the detachable support comprises two or more layers, and the support is dyed with two or more colors is particularly preferable.

A patch of the present invention is produced, for example, by forming an adhesive layer comprising an adhesive composition as explained above on a flexible support. In the present invention, when the adhesive layer comprises two layers of the reservoir layer and the adhering releasing layer, the reservoir layer is arranged near the support, and the adhering releasing layer is arranged at the side where the patch is applied on the skin. Commonly, the reservoir layer and the adhering releasing layer are directly pressed and brought to contact with each other. However, an intermediate layer having no effect on the releasability may be present between them. The other side of the reservoir layer which is free from the contact with the adhering releasing layer may be directly pressed onto the support, or may be pressed onto the support through another bonding agent or pressure sensitive adhesive. When such intermediate layer exists, it is preferable that the intermediate layer scarcely absorbs isosorbide dinitrate, and if absorbs, the reservoir layer may contain more isosorbide dinitrate, taking the amount of absorption by the intermediate layer into account beforehand.

In the present invention, in order to produce a patch having two or more layers comprising the reservoir layer and the adhering releasing layer, the reservoir layer and the adhering releasing layer each having an adjusted concentration of isosorbide dinitrate are prepared at first, and an adhesive layer is formed, for example, on a support by laminating these layers.

However, an example of a more preferable method in view of cost is as follows: at first, a reservoir layer is prepared by compounding isosorbide dinitrate in an amount including the amount to move to an adhering releasing layer, that is, a reservoir layer containing 22 to 45% isosorbide dinitrate is prepared; on the other hand, an adhering releasing layer containing completely no or only a small amount of isosorbide dinitrate is formed; these two layers are laminated directly or through another layer; and subsequently they are heated at a temperature of 40 to 100° C. to move the isosorbide dinitrate from the reservoir layer to the adhering releasing layer. The amount of the move of isosorbide dinitrate depends on temperature and time, and they are heated preferably at 40 to 60° C. for 8 to 48 hr. When heated particularly at 40 to 45° C., they can produce a product having a constant property with such a wide allowance of heating time as 20 hr to 1 week.

Further, another mode for enhancing the effect of the present invention is achieved by a patch in which an adhesive layer composed of an adhesive composition is formed on a flexible support; the adhesive composition comprises the acrylic-based adhesive (A), the polyvinyl acetate-based adhesive (B), the plasticizing component (C) and isosorbide dinitrate (D); and weight ratios of each of the components satisfy the following (1) through (4):

(1) A:B=50:50 to 10:90,
(2) the ratio of C based on the adhesive composition is 20 to 40% by weight,
(3) the ratio of D based on the adhesive composition is 20 to 30% by weight, and
(4) water content based on the adhesive composition is 0.5% or less by weight.

The function of a patch of the present invention can be further stimulated by suppressing the water content of the adhesive composition below a specified level. In particular, when the water content of the adhesive composition is 0.5% or less, more preferably 0.2% or less by weight, the remarkable function will be attained.

In many of conventional isosorbide dinitrate-containing patches, isosorbide dinitrate is deposited as crystals while they are applied on the skin. However, on the other hand, it is known that isosorbide dinitrate has a relatively high level of percutaneous absorption in an isosorbide dinitrate-containing patch. This is owing to the fact that even in the case where the crystals of isosorbide dinitrate deposit, the crystalline isosorbide dinitrate easily dissolves again when the concentration of isosorbide dinitrate in the adhesive composition decreases by percutaneous absorption, and resultingly the percutaneous absorption is kept for a long time.

However, for achieving a far higher level of percutaneous absorption than the conventional patches, this being the object of the present invention, the higher the concentration of the isosorbide dinitrate dissolved in the adhesive composition is, the more preferable it will be. Further, it is preferable to contrive so that the activity of the isosorbide dinitrate in such a high dissolved state is enhanced when the patch is applied on the skin.

As mentioned above, even in the system where the crystals of isosorbide dinitrate are deposited in the adhesive composition, for example, even in a single-adhesive system where the crystals of isosorbide dinitrate are deposited in an acrylic-based adhesive (A), the percutaneous absorption is stimulated by adding a plasticizing component (C). However, a patch of the present invention exhibits a far higher level of percutaneous absorption than said single-adhesive system. Moreover, in the patch of the present invention, which can demonstrate a high level of percutaneous absorption, a further higher level of percutaneous absorption is achieved when the water content of the adhesive composition is kept not more than 0.5%.

Namely, the inventors of the present invention found that when a water content in an adhesive composition is suppressed to 0.5% or less by weight, a solubility of isosorbide dinitrate in the adhesive composition is increased, and moreover when the patch is applied on the skin and water comes into the adhesive composition from the living body, the activity of the dissolved isosorbide dinitrate in the patch is enhanced and the absorption is further increased.

Further, it was surprisingly found that in an adhesive composition of the present invention, even when the water content is increased by the application, isosorbide dinitrate does not deposit as crystals in the adhesive composition, and furthermore crystals of isosorbide dinitrate hardly deposit even during application, supposedly owing to the fact that the movement of the agent tending to crystallize results in the acceleration of percutaneous absorption.

A water content in an adhesive composition, in the present invention, means a water content in the pressure-sensitive adhesive when a patch is mainly composed of a pressure-sensitive adhesive, but it should be determined based on the total weight when the pressure-sensitive adhesive is attached with a support and plaster surface-covering material whose weight is heavier than that of the pressure-sensitive adhesive.

In the case of an ordinary acrylic-based adhesive, an isosorbide dinitrate-containing patch is prepared by using a non-aqueous solvent such as ethyl acetate. Namely, an ethyl acetate solution of the acrylic-based adhesive containing isosorbide dinitrate is cast on a liner or support, and the product is dried to obtain an isosorbide dinitrate-containing patch. In this case, just after the coating, the water content in the patch might be not higher than 0.5%. However, since the equilibrium water content of an acrylic-based adhesive is 1% or more by weight under ordinary conditions, and moreover a patch is a film as thin as 10 to 100 $\mu$m, it is not easy to keep the water content at 0.5% or less by weight under ordinary conditions, and hence, for example, when a patch is manufactured under insufficient control of the water content or when package is not specially contrived, a stable patch is hardly obtained. In an isosorbide dinitrate-containing patch, the combination, which is proposed in the present invention, of an adhesive composition having such a high compatibility with isosorbide dinitrate and the suppression of water content as a means for heighten the compatibility has not been known so far.

In the production of patches of the present invention, the water content can be reduced by subjecting isosorbide dinitrate-containing patches obtained by an ordinary coating to heat treatment, reduced pressure treatment, etc. However, a particularly preferable method for manufacturing patches is composed of the first through third processes shown bellow.

The first process: an adhesive layer of one or not less than two layers [(L1) or (L1 and L2)], in which weight ratios of an acrylic-based adhesive (A), a polyvinyl acetate-based adhesive (B) and a plasticizing component (C) satisfy the following (1) and (2), and isosorbide dinitrate is not contained or contained only in a small amount, is produced beforehand.

(1) A:B=50:50 to 10:90, and
(2) the ratio of C based on the adhesive composition is 25 to 57% by weight.

The second process: a fabric having 8 to 3 unit area weight and the adhesive layer(s) [(L1) or (L1 and L2)] containing only a small amount of isosorbide dinitrate are laminated or a fabric having 8 to 30 g/m$^2$ unit area weight and the adhesive layer (L1) free from isosorbide dinitrate are laminated to produce a laminated fabric. An isosorbide dinitrate (D) solution of a solvent such as acetone, ethyl acetate or ethanol is used to impregnate the resultant laminated fabric, for example, with a method such as coating or spraying, and the solvent is removed so that the isosorbide dinitrate (D) is contained in the fabric. When the other adhesive layer (L2) exists, it is laminated under pressure on the laminated fabric. Thus, a raw fabric of patch comprising a laminate which contains isosorbide dinitrate is produced.

The third process: after or before the cutting process of the raw fabric of patch containing the isosorbide dinitrate (D) obtained in the second process, the water content in the patch is reduced to 0.5% or less by weight through a heat treatment and/or a reduced pressure treatment, and the product is sealed according to demand.

A flexible materials which from the support of the present invention can be laminated on one of the free side of the adhesive layer in the first process among the above three processes. Further, by passing through these three processes, weight ratios of each of the components in the adhesive composition resultingly come into the above-mentioned numerical ranges of the present invention.

In addition, "a small amount" in the first process means an amount less than required for exhibiting expected drug action as an isosorbide dinitrate-containing patch, or a proximity of amount in which drug action is not exhibited nor do crystals deposit, for example, not more than 5% or not more than 10%.

The isosorbide dinitrate (D), mainly existing in the fabric of the patch obtained through these processes, is diffused into the whole laminated adhesive layer by heat treatment, etc., and this heat treatment can be carried out before seal-packaging in a state of raw fabric or after cutting of patch, or can be carried out together with the packaging bag after seal-packaging.

Since the adhesive composition of the present invention contains large amount of a liquid component, i.e. plasticizing component (C), it is difficult to remove a residual solvent which is considered to cause problems on safety. Furthermore, it is required to remove only solvent without subliming isosorbide dinitrate (D) in spite that isosorbide dinitrate (D) is sublimable, and it is extremely difficult to reconcile both requirement in the manufacturing process.

However, in a preferable manufacturing method of the present invention, the residual solvent can be sufficiently removed from the adhesive composition on the process where an adhesive composition containing only a small amount of or free from isosorbide dinitrate (D) is produced, and therefore no treatment is required other than the treatment for removing only the solvent used for the impregnation with isosorbide dinitrate (D) in the second process. The removal of this solvent is widely improved by reducing the amount of the solvent used in the second process or using a solvent having high volatility.

The water content in the adhesive composition is preferably not more than 0.5%, more preferably not more than 0.2%, and particularly more preferably not more than 0.1% by weight.

In order to constantly obtain a patch composed of an adhesive composition having such a low water content, it is essential to reduce the water content in the adhesive composition on the manufacturing process at first, and in addition, it is preferable that the patch of the present invention is packaged under reduced humidity, under heating or in a stream of dry gas such as nitrogen, and then tightly sealed.

A patch of the present invention can be produced by the above-mentioned manufacturing processes. The size of the patch is, for example, 30 cm$^2$ or less, preferably 10 to 27 cm$^2$.

Incidentally, an isosorbide dinitrate-containing patch is used mainly for angina pectoris, which many senile patients suffer from, and therefore the handleability is an important factor in the patch. A patch of the present invention is sufficiently small in size and high in safety. However, there is another mode of a patch in which the handleability is further greatly improved as shown bellow. For example, when a patch (a patch having a size of 30 cm$^2$ or less) of the present invention is placed with the surface of a plaster surface-covering material (a separating liner) on the upside in such a state that the center of the patch comes at the origin of an X-Y rectangular coordinate plane, a splitting line for splitting the plaster surface-covering material of the patch passes the fourth quadrant, the first quadrant and the second quadrant, and the splitting line extends in the minus direction in terms of the X-coordinate as long as a half (X2/2) or longer of the length (X2) of the minus X-coordinate to the edge of the patch in the minus direction in the second quadrant, and in addition the splitting line splits the total area of the second quadrant and the third quadrant at the ratio of 2:1 or less.

Commonly, a bipartite plaster surface-covering material is placed on a patch, and for applying the patch on the skin, one piece of the split plaster surface-covering materials is removed, and then the patch is applied. If the patch is too flexible, when the piece of the split plaster surface-covering material is removed, the bare adhesive layer becomes curled, and it is not easy to handle. If a hard support is used, the curling is suppressed, but skin irritation becomes serious. The inventors of the present invention considered that for solving this problem, it would be effective to improve the plaster surface-covering material, which is used only on handling, and they studied on this matter and reached the above-mentioned preferable mode. Namely, the inventers found that when one piece of the plaster surface-covering material is removed, the patch must be easily applicable, and accordingly when one piece of the plaster surface-covering material is removed, it is better that there is no exposed adhesive layer in the third quadrant and further the adhesive layer is little in the second quadrant. In common patches, no plaster surface-covering material is left in the second and the third quadrants when one piece of the plaster surface-covering material is removed for applying, or the splitting line is moved toward the second and third quadrants along a parallel line to the Y-coordinate. But, this cannot solve the problem of curling. In addition, it becomes difficult to apply. Thereby, it was found that the curling problem is widely improved if there is no plaster surface-covering material in the third quadrant and the plaster surface-covering material is little in the second quadrant when one piece of the plaster surface-covering material is removed as mentioned above, and in addition the plaster surface-covering material in the second quadrant is moved out toward the minus X-coordinate.

As explained above, an isosorbide dinitrate-containing patch of the present invention can greatly satisfy the requirement of a high level of percutaneous absorption and a sufficient adhesive strength enabling the stable application at the same time, although such a high performance was not attained in conventional patches.

Some commercial patches containing 40 mg of isosorbide dinitrate have an area of 30 cm$^2$, but most products have an area of 40 cm$^2$ or more. On the other hand, a patch of the present invention is 27 cm$^2$ or less in area, and further even a patch of 20 cm$^2$ or less is possible in the present invention.

EXAMPLES

The following provides a more detailed explanation of the present invention through examples. Parts, percentages and ratios in the examples are all based on weight.

The measurement of blood isosorbide dinitrate concentration, and the preparation of a polyvinylacetate-based adhesive, an acrylic-based adhesive and a fabric sample used in the examples are as indicated below.

(1) Measurement of Blood Isosorbide Dinitrate (later, this is sometimes abbreviated as ISDN) Concentration After separating the plasma from 1 ml of sampled whole blood, ISDN is extracted using 4 ml of n-hexane followed by concentration and the addition of 100 $\mu$l of ethyl acetate to the concentrate to obtain the sample. The amount of ISDN in the sample is assayed by GC-ECD.

(2) Preparation of Polyvinyl Acetate-Based Adhesive Solution (B-dope)

Seventy parts of vinyl acetate (Wako Pure Chemical Industries Ltd.), 27 parts of 2-ethylhexyl acrylate, 3 parts of acrylic acid, 1 part of benzoyl peroxide and 150 parts of ethyl acetate were charged into a reaction vessel equipped with a reflux condenser and a stirrer. Polymerization was continued for 12 hours while slowly stirring at 60° C. in a nitrogen atmosphere. The polymerization conversion rate was 99.9%. To the resultant polymer solution, 250 parts of ethyl acetate were added, and the solid concentration was adjusted to about 20% to obtain a polyvinyl acetate-based adhesive solution. In the obtained vinyl acetate-based adhesive, the weight average molecular weight (converted into that of polystyrene) was 510,000, the number average molecular weight (Mn) was 78,000 and the residual monomer content was 1% or less.

(3) Preparation of Acrylic-Based Adhesive (AP) Solution (A-dope)

Ninety parts of 2-ethylhexyl acrylate, 7 parts of methacrylic acid, 3 parts of acrylic acid, 1 part of benzoyl peroxide and 100 parts of ethyl acetate were charged into a reaction vessel equipped with a reflux condenser and a stirrer. Polymerization was continued for 10 hours while slowly stirring at 60° C. in a nitrogen atmosphere. The polymerization conversion rate was 99.9%. To the resultant polymer solution, 500 parts of ethyl acetate were added, and the solid concentration was adjusted to about 20% to obtain a acrylic-based adhesive solution. The weight average molecular weight (Mw) of the obtained acrylic-based adhesive was 585,000.

(4) Preparation of Fabric Sample

In a glass flask equipped with a fractionating column, 297 parts of dimethyl terephthalate, 265 parts of ethylene glycol, 53 parts of sodium 3,5-di(carbomethoxy)benzenesulfonate (11.7 mol % of dimethyl terephthalate), 0.084 parts of $Mn(CH_3COO)_2 \cdot 4H_2O$ and 1.22 parts of $NaCH_3COO \cdot 3H_2O$ were placed. After performing transesterification in accordance with the usual method and distilling off the theoretical amount of methanol, the reaction product was transferred into a polycondensation flask equipped with a fractionating column followed by the addition of 0.090 part of a 56% aqueous solution of orthophosphoric acid as a stabilizer and 0.135 pat of antimony trioxide as a polycondensation catalyst. After reacting at 275° C. for 20 minutes under normal pressure and then for 15 minutes under reduced pressure of 30 mmHg, the reaction was continued for 100 minutes under high vacuum. The final internal pressure was 0.39 mmHg, the intrinsic viscosity of the resultant copolymer was 0.402, and the softening point was around 200° C. After completing the reaction, the copolymer was formed into chips in accordance with a usual process.

After mixing 15 parts of these polymer chips with 85 parts of polyethylene terephthalate chips having an intrinsic viscosity of 0.640 in a Nauta mixer (produced by Hosokawa Ironworks) for 5 minutes, the mixture was dried in a nitrogen atmosphere for 2 hours at 110° C. and then for 7 hours at 150° C. followed by melting and kneading at 285° C. using a twin-screw extruder into chips. The intrinsic viscosity of the chips was 0.535, and the softening point was 261° C.

The chips were dried in a usual manner and then spun through a spinneret having arc-shaped openings formed by closing two places of a circular slit of 0.05 mm in width and 0.6 mm in diameter in a usual manner to produce hollow fibers having a ratio of outer diameter to inner diameter of 2:1 (hollow rate: 25%).

The resultant hollow fiber had fine pores dispersed over the entire cross-sectional surface of said hollow fiber and arranged in the direction of the fiber. At least a portion of said fine pores were connected to the hollow portion of the fiber. The yarn was composed of 300 denier/24 filaments, and was drawn at an elongation ratio of 4.2 in accordance with a usual manner to obtain a multifilament yarn of 71 denier/24 filaments. A single filament of this multifilament yarn had a diameter of 11 $\mu$m.

This multifilament yarn was formed into a Merrius knitted fabric, and after scouring and drying in accordance with routine methods, the fabric was treated with 1% aqueous caustic soda at boiling temperature for 2 hours to obtain a knitted fabric having an alkaline thinning rate of 20%. The resultant knitted fabric was drawn by 1.5 times longitudinally and thermoset at 100° C. for one minute to produce a knitted fabric having 17 g/m$^2$ unit area weight, namely the fabric sample.

Example 1

After 87.5 parts of the polyvinyl acetate-based adhesive solution (dope B), 87.5 parts of the acrylic-based adhesive solution (dope A), 35 parts of isopropyl myristate (C), 30 pars of isosorbide dinitrate (D), 193 parts of ethyl acetate and 0.14 part of aluminum acetylacetonate were mixed to almost homogeneous state, the resultant mixture was used for coating a polyethylene terephthalate separator (Japanese Pharmaceutical Excipients) 75 $\mu$m thick in such a state so as to have a thickness of 45 $\mu$m after drying and sufficiently dried so that the residual ethyl acetate became 100 ppm or less to obtain a reservoir layer. A polyethylene terephthalate film (PET film) 2.0 $\mu$m thick (Teijin Film Type F3) was pressed to adhere onto the free surface of the reservoir layer 45 $\mu$m thick containing 30% isosorbide dinitrate by weight.

Separately, after 117.5 parts of the dope B, 117.5 parts of the dope A, 35 parts of isopropyl myristate (C) and 18 parts of isosorbide dinitrate (D) were mixed to almost homogeneous state, the resultant mixture was used for coating a polyethylene terephthalate separator (Japanese Pharmaceutical Excipients) 75 $\mu$m thick in such a state so as to have a thickness of 15 $\mu$m after drying and sufficiently dried so that the residual ethyl acetate became 100 ppm or less. Thus, an adhering releasing layer 15 $\mu$m thick containing 18 parts of isosorbide dinitrate was obtained.

Subsequently, while peeling the polyethylene terephthalate separator from the reservoir layer prepared above, the free surface of the adhering releasing layer 15 $\mu$m thick was pressed to adhere onto the bare adhesive surface.

Thus, a raw fabric of patch, composed of a 2.0 $\mu$m PET film, a reservoir layer 45 $\mu$m thick, an adhering releasing layer 15 $\mu$m thick and a polyethylene terephthalate separator 75 $\mu$m thick from the outside, was obtained. The raw fabric of patch was cut to a size of 25 cm$^2$ (3.5 cm long and 7.1 cm wide) to obtain a patch (TC-1) of 25 cm$^2$ in size containing 40 mg of isosorbide dinitrate.

The TC-1 was divided into four equal parts to obtain pieces of testing patch of 6.25 cm$^2$ in size. This testing patch was applied on the shaved back of mail hairless rats (n=4, a mean body weight of 165 g) of 8 weeks old. Blood samples of about 1.0 ml a time were withdrawn from the tail before application, and 2 hr and 5 hr after application, plasmas were separated from the samples, and the concentrations of isosorbide dinitrate in the plasmas were determined (n=4). Resultingly, the concentrations before application, and 2 hr and 5 hr after application were 0, 1244 and 938 ng/ml, respectively, and AUC was 4517 ng.hr/ml.

In addition, the adhesive strength of TC-1 was determined according to an adhesive strength testing method of plaster of Japanese Pharmacopoeia, and it was 100 g/12 mm. As a result of the application of TC-1 on hairless rats, no skin irritation was observed and there was no "remaining adhesive", and the result was good as a whole. The results are shown in Table 1. In the table, "reservoir" means a reservoir layer, "releasing" means an adhering releasing layer, and AUC ratios are expressed based on the AUC of a patch in comparative example 1 described later. Further, when "remaining adhesive" was observed, the box is marked with "present", and when no "remaining adhesive" was detected, nothing is marked in the box.

TABLE 1

| Experiment No | | Composition (%) | | | | Thickness ($\mu$m) | Adhesive Strength (g/12 min) | Remaining Adhesive | AUC Ratio |
| --- | --- | --- | --- | --- | --- | --- | --- | --- | --- |
| | | A | B | C | D | | | | |
| Comp. Ex. 1 | simple | 80 | — | — | 20 | 80 | 200 | | 1.0 |
| Comp. Ex. 2 | simple | 70 | — | — | 30 | 53 | 150 | | 0.9 |
| Comp. Ex. 3 | simple | 50 | — | 30 | 20 | 80 | 70 | | 1.9 |
| Comp. Ex. 4 | simple | 40 | — | 30 | 30 | 53 | 30 | | 1.7 |
| Comp. Ex. 5 | simple | — | 80 | — | 20 | 80 | 60 | | 1.1 |
| Comp. Ex. 6 | simple | — | 70 | — | 30 | 53 | 60 | | 1.3 |
| Comp. Ex. 7 | simple | — | 50 | 30 | 20 | 80 | 10 | present | 1.6 |
| Comp. Ex. 8 | simple | — | 40 | 30 | 30 | 53 | 10 | present | 2.4 |
| Comp. Ex. 9 | simple | 21 | 49 | — | 30 | 53 | 70 | | 1.3 |

TABLE 1-continued

| Experiment No | | Composition (%) | | | | Thickness ($\mu$m) | Adhesive Strength (g/12 min) | Remaining Adhesive | AUC Ratio |
|---|---|---|---|---|---|---|---|---|---|
| | | A | B | C | D | | | | |
| Comp. Ex. 10 | simple | 21 | 49 | 10 | 20 | 53 | 80 | | 1.7 |
| Example 3 | simple | 12 | 28 | 30 | 30 | 53 | 30 | | 2.8 |
| Example 4 | simple | 17.5 | 17.5 | 35 | 30 | 53 | 40 | | 2.5 |
| Example 1 | reservoir | 17.5 | 17.5 | 35 | 30 | 45 | 100 | | 3.5 |
| | releasing | 23.5 | 23.5 | 35 | 18 | 15 | | | |
| Example 2 | reservoir | 15 | 15 | 40 | 30 | 45 | 70 | | 4.1 |
| | releasing | 21 | 21 | 40 | 18 | 15 | | | |

Example 2

With the exception that the amount of isopropyl myristate in adhesive composition was change to 40 parts from the 35 parts in Example 1 and the weight ratios of the other components were adjusted as shown in Table 1, an isosorbide dinitrate-containing patch (TC-2) was prepared in the same manner as Example 1, and the obtained patch was evaluated also in the same manner as Example 1. The results are shown in Table 1. It shows that there was a tendency for the adhesive strength to slightly decrease, but the level of percutaneous absorption was higher than Example 1.

Example 3

After 60 parts of the dope B, 140 parts of the dope A, 30 parts of isopropyl myristate (C), 30 pars of isosorbide dinitrate (D), 140 parts of ethyl acetate and 0.16 parts of aluminum acetylacetonate were mixed to almost homogeneous state, the resultant mixture was used for coating a polyethylene terephthalate separator (Japanese Pharmaceutical Excipients) 75 $\mu$m thick in such a state so as to have a thickness of 53 $\mu$m after drying and sufficiently dried so that the residual ethyl acetate became 100 ppm or less to obtain an adhesive.

A polyethylene terephthalate film 2.0 $\mu$m thick (Teijin Film Type F3) was pressed to adhere onto the free surface of the adhesive layer containing 30% isosorbide dinitrate by weight to obtain a raw fabric of patch. The raw fabric of patch was cut to a size of 25 cm$^2$ (3.5 cm long and 7.1 cm wide) to obtain a patch (TC-3) of 25 cm$^2$ in size containing 40 mg of isosorbide dinitrate. Regarding TC-3, same evaluations as Example 1 were carried out, and the results are shown in Table 1.

Example 4 and Comparative Examples 1 to 10

The weight ratios of A, B, C and D of Example 3 being changed into those shown in Table 1, patches (Example 4 and Comparative Examples 1 to 10) were obtained in the same manner as Example 3, and the results of evaluations are shown in Table 1.

It can be understood from the results of Experiments 1 to 4 that as shown in Table 1, specific combinations of A, B, C and D gave an extremely high level of percutaneous absorption, and particularly under the conditions of Experiments 1 and 2, patches gave high levels of percutaneous absorption and at the same time gave sufficiently large adhesive strengths. On the other hand, the results of Comparative Experiments 1 to 10 showed the following facts. For example, even if ISDN was dissolved at high concentrations in B, percutaneous absorption speeds were not increased directly proportionally to the increase in the concentrations in B, and this might be owing to the fact that the diffusion speed of ISDN in B is not large. In addition, when C was added to B at high concentrations, levels of percutaneous absorption were increased, but the increasing ratios were relatively small. Also, the adhesive strength of B was originally weak and further lowered when the concentration of C was increased, and this caused the trouble such as "remaining adhesive" and demonstrated the difficulties of obtaining stable patches. Further, although the level of percutaneous absorption became high when A and B were combined, the effect of the combination on percutaneous absorption was considerably small comparing with that of patches of the present invention.

Experiment 5

The dope A was used for coating polyethylene terephthalate separators 75 $\mu$m thick in such a manner so as to have a thickness of 10 $\mu$m after drying and sufficiently dried to obtain sheets of an adhesive layer (LA layer) for lamination having a thickness of 10 $\mu$m.

One sheet of the LA layer was pressed to adhere onto the free surface of 2.0 $\mu$m thick polyethylene terephthalate film layer of the raw fabric of patch obtained in Example 1, then the fabric sample was pressed to adhere onto the free surface of the LA layer, further another sheet of the LA layer was pressed to adhere onto the free surface of the fabric sample, and 2.0 $\mu$m thick polyethylene terephthalate film was pressed to adhere on the free surface of this LA layer. Subsequently, the resultant raw fabric of patch was cut to a size of 25 cm$^2$ to obtain a patch (TC-5).

Evaluations same as those on Example 1 were carried out on TC-5, and it was found that the level of percutaneous absorption was 1.12 times that of the sample in Example 1 in terms of AUC, but adhesive strength was hardly changed.

TC-5 demonstrated better handleability on application to and removal from the skin than TC-1.

Example 6

A patch (TC-6) was prepared in the same manner as Example 5 by using 1.3 $\mu$m thick polyethylene terephthalate film in place of 2.0 $\mu$m thick polyethylene terephthalate film in Example 5, and the patch was evaluated in the same manner as Example 5. TC-6 did not show significant difference in percutaneous absorption and adhesive strength, but it was more flexible than TC-5, and TC-6 was more favorable in view of the present invention.

Example 7

Dope A was compounded with isopropyl myristate and aluminum acetylacetonate in amounts of 35% and 4% of the solid component in the dope A, respectively, and the resultant dope was used for coating in such a manner so as to have a thickness of 10 $\mu$m after drying to obtain an adhesive layer.

A flesh-colored bulky fabric sample knitted so as to have a unit area weight of 55 g/m² was attached on one side of the resultant adhesive layer to obtain a product, which is hereafter called supporter.

The free surface of adhesive layer of the supporter was pressed to adhere onto the free surface of the 2.0 μm thick polyethylene terephthalate film of the raw fabric of patch obtained in Example 1.

Thus obtained raw fabric of patch was cut to a size of 25 cm² to obtain a patch (TC-7).

In TC-7, the 2.0 μm thick film and the supporter could be freely attached on or separated from each other. Accordingly, while a patch was being applied on the skin, the supporter was attached on the patch, this enabling easy handling. Then, on use, the supporter was removed, this enabling the maximum demonstration of strong points such as flexibility, resistance to peeling and high stability, which is characteristic to a film-type preparation.

Example 8

In Example 7, a supporter was attached on the free surface of a 2 μm thick polyethylene terephthalate film in a single layer. In this example, the size of a patch was 3.5 cm×7.1 cm, and supporters were two kinds of white 3.5 cm×4.5 cm sheet and red 3.5 cm×4.5 cm sheet. The red supporter was attached on the 2 μm thick polyethylene terephthalate film from one edge, the white supporter was attached on it from the opposite edge, and the white supporter came at upper side at the position where the both supporters overlap each other. Thus, a supporter-type patch similar to that of Example 7 was obtained. Being particularly excellent in handleability, the patch of Example 8 was a preferable one.

Example 9

With the exception of using ethyl oleate in place of isopropyl myristate, a patch was prepared in the same manner and with same objects as Example 1, and the obtained patch was evaluated.

Resultingly, almost no difference was observed between the patch using isopropyl myristate and that using ethyl oleate.

Example 10

A patch was prepared by using a 1.3 μm thick polyethylene terephthalate film (Teijin Film Type HF) in place of the 2.0 μm thick one in Example 8, and the obtained patch was evaluated.

As the result, this patch demonstrated no differences in percutaneous absorption and handleability from the patch of Example 8. However, the patch of Example 10 was further more flexible than the patch of Example 8 and exhibited extremely little foreign feeling.

Example 11

After 174 parts of the polyvinyl acetate-based adhesive solution (dope B), 31 parts of the acrylic-based adhesive solution (dope A), 35 parts of isopropyl myristate (C), 24 pars of isosorbide dinitrate (D), 130 parts of ethyl acetate, 0.04 part of aluminum acetylacetonate and 4 parts of acetyl acetone were mixed to almost homogeneous state, the resultant mixture was used for coating polyethylene terephthalate separators (Japanese Pharmaceutical Excipients) 75 μm thick so as to obtain two adhesive layers having a thickness of 29 μm (L1) and a thickness of 59 μm (L2) after drying, each containing 24% isosorbide dinitrate.

Subsequently, these two adhesive layers (L1 and L2), a 2.0 μm thick polyethylene terephthalate film (Teijin Film Type F3) and the fabric sample were pressed with a pressure of 4 kg/cm² G to adhere them in the order of the polyethylene terephthalate film, the adhesive layer L1, the fabric sample, the adhesive layer L2 and the polyethylene terephthalate separator from the outermost layer to obtain a raw fabric of patch. The raw fabric of patch was punched out into rectangles (major axis of 57 mm, minor axis of 35 mm) of 18 cm in area having four rounded corners, patches were heated at 70° C. for 24 hr to reduce the water content of the whole patch down to 0.09%, and each patch was sealed quickly in a four side-sealed aluminum bag of 8 cm×9 cm in size contriving the protection of the patch from getting moistened. In the patch thus obtained of 18 cm² in size containing 40 mg of isosorbide dinitrate, the isosorbide dinitrate existed in a dissolved state (crystals were not deposited) in the adhesive composition, and no crystal deposition was observed even after 6 months or longer.

A patch of the present invention, which were packed under protection from getting moistened to keep water content at 0.09% as it was, was divided into four equal parts of 4.5 cm² in size. The resultant pieces were subjected to percutaneous absorption tests using hairless rats in the same manner as Example 1, and isosorbide dinitrate levels in plasma were determined (n=4). As a result, the levels before application, and 2 hr and 5 hr after application were 0, 1678 and 1305 ng/ml, respectively, and AUC was 6152 ng.hr/ml, and it was clear that the patch was particularly excellent in initial releasing property. The patch exhibited adhesive strength of 107 g/12 mm and little skin irritation, and no "remaining adhesive" were observed on hairless rat tests.

On the other hand, although the water content of the whole patch was 0.09% after preparation, it was exposed to the outer atmosphere for several hours during the work that was carried out in common steps for packaging with a four side-sealing aluminum bag, and the water content became 0.7%. In the case of this patch, crystal deposition was observed in all samples within 1 to 2 weeks. When the patch having crystal deposition was subjected to percutaneous absorption tests, AUC was 3646 ng.hr/ml. It was recognized that by reducing water content through the manufacturing process and further performing packaging under complete moisture proofing conditions, the solubility of isosorbide dinitrate in an adhesive composition of the present invention could be increased, and an extreme improvement of absorption property and long term stability of the patch were achieved.

Further, being tested on adhesive strength according to an adhesive strength testing method for plaster of Japanese Pharmacopoeia, the patch of this Example, whose water content was kept at 0.09% or less, stably exhibited an adhesive strength of 100 to 120 g/12 mm.

Example 12

Figure 2:
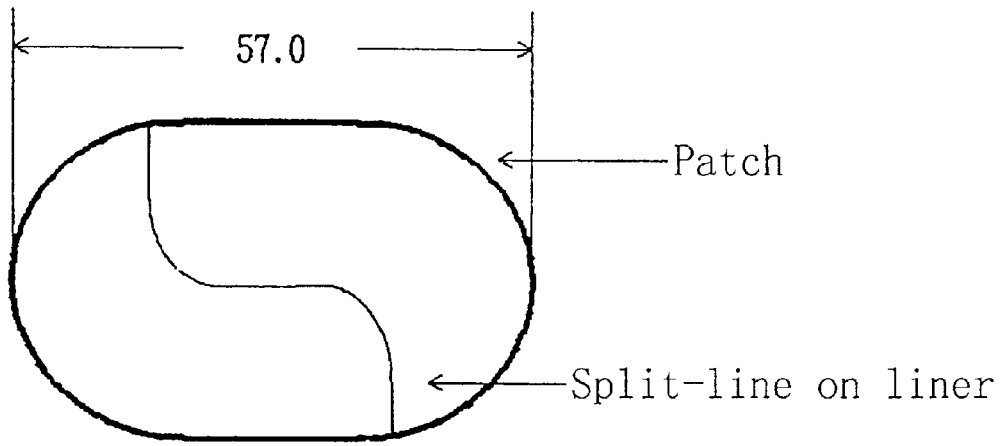
FIG. 2 shows a patch of the present invention prepared in Example 12, and the patch has a major axis of 57 mm and a split-line on liner.

Two kinds of splitting lines were formed as split-line on liner shown in the figures (FIG. 1 and FIG. 2) on the polyethylene terephthalate separators (Japanese Pharmaceutical Excipients), which were the plaster surface-covering materials of patches obtained in Example 11. On both the patches, application tests were carried out in the same manner as ordinary application tests by repeatedly peeling and returning one side of the separator which had been split into two parts by the split-line on liner. As a result, in the case of an ordinary split-line on liner (FIG. 1), when one side of the split separator was peeled, the bared adhesive surface was curling and it was difficult to apply it on the skin. On the other hand, in the case of FIG. 2, in which when the patch was placed so that the center of the patch came at the origin of an X-Y rectangular coordinate, a splitting line passed the fourth quadrant, the first quadrant and the second quadrant, and in addition the splitting line split the total area of the second quadrant and the third quadrant at a specific ratio, no curling was observed even after a number of repetitions of peeling and returning, and it was easy to apply the patch on the skin. Further, in the illustrated FIG. 2, the splitting line deviates somewhat lower side of the figure.

Example 13

After 174 parts of the polyvinyl acetate-based adhesive solution (dope B), 31 parts of the acrylic-based adhesive solution (dope A), 35 parts of isopropyl myristate (C), 130 parts of ethyl acetate, 0.04 part of aluminum acetylacetonate and 4 parts of acetyl acetone were mixed to almost homogeneous state, the resultant mixture was used for coating polyethylene terephthalate separators (Japanese Pharmaceutical Excipients) 75 $\mu$m thick to obtain two adhesive layers having a thickness of 22 $\mu$m (L1) and a thickness of 44.8 $\mu$m (L2) after drying and containing no isosorbide dinitrate.

Subsequently, the adhesive layer (L1), a 2.0 $\mu$m thick polyethylene terephthalate film (Teijin Film Type F3) and the fabric sample were pressed with a pressure of 4 kg/cm$^2$G to adhere them in the order of the polyethylene terephthalate film, the adhesive layer L1 and the fabric sample from the outermost layer to obtain a laminate. Subsequently, a solution prepared by dissolving 24 parts of isosorbide dinitrate in 76 parts of acetone was sprayed almost evenly on the surface of the fabric sample of the laminate to obtain an isosorbide dinitrate-containing laminate. The adhesive layer (L2) was placed on the obtained isosorbide dinitrate-containing laminate in such a manner that the adhesive surface of L2 came into contact with the surface of the fabric sample of the laminate and pressed with a pressure of 4 kg/cm$^2$G to obtain a raw fabric of patch.

The obtained raw fabric of patch was evaluated in the exactly same manner as Example 11 using patches of 18 cm$^2$ in size, and it was recognized that the patches in this example had similar levels of performances to those obtained in Example 11. Further, in the manufacturing method of this example, it was recognized that since a laminate free from isosorbide dinitrate was first produced, even if drying time was made longer than in the manufacturing method of Example 11, there was no danger of the evaporation or decomposition of the isosorbide dinitrate. Accordingly, it became clear that we would be able to produce a patch having little solvent remained in it by this method.

What is claimed is:

1. An isosorbide dinitrate-containing patch, comprising:
   (a) a flexible support; and
   (b) an adhesive layer formed on the flexible support, wherein the adhesive layer comprises an adhesive composition comprising:
      (i) a (meth)acrylic acid alkyl ester-based adhesive (A);
      (ii) a polyvinyl acetate-based adhesive (B), wherein adhesive (B) has a weight average molecular weight range of from 150,000 to 1,000,000;
      (iii) a plasticizing component (C); and
      (iv) isosorbide dinitrate (D);
      and the adhesive composition satisfies the following conditions (1) through (3):
      (1) the weight of (A) to the weight of (B) is from 70:30 to 10:90;
      (2) the weight ratio of (C) based on the weight of the adhesive composition is from 10 to 40%; and
      (3) the weight ratio of (D) based on the weight of the adhesive composition is from 20 to 35%.

2. The isosorbide dinitrate-containing patch as claimed in claim 1, wherein the water has a water content of adhesive composition is 0.5% or less by weight.

3. The isosorbide dinitrate-containing patch as claimed in claim 1, wherein the adhesive layer comprising an adhesive composition is formed on a flexible support, and said adhesive composition comprises a (meth) acrylic acid alkyl ester-based adhesive (A), a polyvinyl acetate-based adhesive (B), a plasticizing component (C) and isosorbide dinitrate (D), and satisfies the weight ratios of each component shown in the following (1) through (4) at the same time:
   (1) A:B=50:50 to 10:90,
   (2) the ratio of C based on the adhesive composition is 20 to 40% by weight,
   (3) the ratio of D based on the adhesive composition is 20 to 30% by weight, and
   (4) the water content in the adhesive composition is 0.5% or less by weight.

4. The isosorbide dinitrate-containing patch as claimed in claim 1, wherein the patch has a size of less than 30 cm$^2$ and a plaster surface-covering material is present on its free surface, and when the patch is present with the surface of the plaster surface-covering material on the upside in such a state that the center of the patch comes at the origin of an X-Y rectangular coordinate plane, a splitting line for splitting the plaster surface-covering material passes the fourth quadrant, the first quadrant and the second quadrant, and the splitting line extends in the minus direction in terms of the X-coordinate as long as a half (X2/2) or longer of the length (X2) of the minus X-coordinate to the edge of the patch in the second quadrant, and in addition the splitting line splits the total area of the second quadrant and the third quadrant at the ratio of (not less than 2):(not more than 1).

5. The isosorbide dinitrate-containing patch as claimed in claim 1, wherein the plasticizing component (C) is a saturated or unsaturated fatty acid having 12 or more carbon atoms, or is an ester of said fatty acid.

6. The isosorbide dinitrate-containing patch as claimed in claim 1 or 5, wherein the thickness of said adhesive layer is 50 to 120 $\mu$m.

7. The isosorbide dinitrate-containing patch as claimed in claim 1 or 5, wherein said flexible support is a polyester film which is water-semipermeable, 8 to 100 g/mm in strength in each of two directions which are substantially perpendicular to each other, 30 to 150% in elongation in each of the two directions which are substantially perpendicular to each other, 1.0 to 4.0 in the ratio of elongations in, two directions (when the elongations in the two directions are different from each other, the smaller one is in the denominator) and 0.5 to 4.9 $\mu$m in thickness.

8. The isosorbide dinitrate-containing patch as claimed in claim 1 or 5, wherein said flexible support comprises a polyethylene terephthalate film which is water-semipermeable, 8 to 100 g/mm in strength in each of two directions which are substantially perpendicular to each other, 30 to 150% in elongation in each of two directions which are substantially perpendicular to each other, 1.0 to 4.0 in the ratio of elongations in the two directions (when the elongations in the two directions are different from each other, the smaller one is in the denominator) and 0.5 to 4.9 $\mu$m in thickness, and the following (1) and (2) are satisfied:
   (1) the thickness of said adhesive layer is 60 to 100 $\mu$m, and (2) the size of the patch is 10 to 27 cm² and the isosorbide dinitrate content in the patch is about 40 mg.

9. The isosorbide dinitrate-containing patch as claimed in claim 1 or 5, wherein said flexible support is a laminated support prepared by laminating components selected from the following (a) through (e):
   (a) the outermost film layer 0.5 to 100 μm thick,
   (b) a bonding layer 1 to 100 μm thick,
   (c) a fabric,
   (d) a bonding layer 1 to 100 μm thick, and
   (e) a film layer 0.5 to 100 μm thick,
in the following order from the outermost layer: (a), (b), (c), (d) and (e); (a), (c), (d) and (e); (a), (b), (c) and (e); (c), (d) and (e); or (a), (b) and (c).

10. The isosorbide dinitrate-containing patch as claimed in claim 1 or 5, wherein said flexible support is a support containing an easily removable supporter composed of materials colored with two or more different colors.

11. The isosorbide dinitrate-containing patch as claimed in claim 1 or 5, wherein the polyvinyl acetate-based adhesive (B) is a pressure-sensitive adhesive comprising a copolymer of:
   a vinyl acetate; and
   a (meth)acrylate acid alkyl ester and/or (meth)acrylic acid, wherein a copolymerization ratio of the vinyl acetate is at least 50% by weight.

12. The isosorbide dinitrate-containing patch as claimed in claim 1 or 5, wherein the (meth)acrylic acid alkyl ester-based adhesive (A) is a copolymer of (meth)acrylic acid alkyl ester and an acrylic acid and/or (meth)acrylic acid whose copolymerization ratio is at least 50% by weight, wherein the alkyl group of the (meth)acrylic acid alkyl ester has an average of 4 or more carbon atoms.

13. The isosorbide dinitrate-containing patch as claimed in claim 1 or 5, wherein:
   the adhesive layer comprises at least two layers, including:
      a reservoir layer; and
      an adhering releasing layer arranged at a human skin side of the patch,
      wherein the reservoir layer has a thickness of 10 to 100 μm and comprises an adhesive composition satisfying the following conditions (1) through (3):
         (1) the weight of (A): the weight of (B)=60:40 to 10:90;
         (2) the weight ratio of (C) based on the weight of the adhesive composition of the reservoir layer is 20 to 40%; and
         (3) the weight ratio of (D) based on the weight of the adhesive composition of the reservoir layer is 25 to 35%,
      and wherein the adhering releasing layer has a thickness of 3 to 25 μm and comprises an adhesive composition satisfying the following conditions (1) through (3);
         (1) the weight of (A): the weight of (B)=0:100 to 100:0;
         (2) the weight ratio of (C) based on the weight of the adhesive composition of the adhering releasing layer is 0 to 40%; and
         (3) the weight ratio of (D) based on the weight of the adhesive composition of the adhering releasing layer is 10 to 30%.

14. A method for manufacturing an isosorbide dinitrate-containing patch, comprising:
   (1) forming an adhesive layer, wherein the adhesive layer has a thickness of from 50 to 120 μm and comprises an adhesive composition comprising:
      (A) a (meth)acrylic acid alkyl ester-based adhesive;
      (B) a polyvinyl acetate-based adhesive, wherein said polyvinyl acetate-based adhesive has a weight average molecular weight range of from 150,000 to 1,000,000;
      (C) a plasticizing component; and
      (D) isosorbide dinitrate;
      wherein the adhesive composition satisfies the following conditions (I) through (III):
         (I) the weight of (A) to the weight of (B) is from 70:30 to 10:90;
         (II) the weight ratio of (C) based on the weight of the adhesive composition is from 10 to 40%; and
         (III) the weight ratio of (D) based on the weight of the adhesive composition is from 20 to 35%; and
   (2) laminating the adhesive layer to a flexible support, wherein the flexible support comprises a fabric having 5 to 60 g/m² unit area weight.

15. The method of claim 14, wherein the conditions (I) through (III) satisfied by the adhesive composition are:
   (I) the weight of (A) to the weight of (B) is from 50:50 to 10:90;
   (II) the weight ratio of (C) based on the weight of the adhesive composition is from 20 to 40%; and
   (III) the weight ratio of (D) based on the weight of the adhesive composition is from 20 to 35%.

16. The method of claim 14, further comprising the following step (3):
   (3) applying a heat treatment or a reduced pressure treatment to the isosorbide dinitrate-containing patch to reduce the water content of the patch to 0.5 wt % or less.

17. A method for manufacturing an isosorbide dinitrate-containing patch, comprising:
   (1) forming an adhesive layer, wherein the adhesive layer comprises at least two layers comprising:
      (i) a reservoir layer arranged at a flexible support side of the patch; and
      (ii) an adhering releasing layer arranged at a human skin side of the patch, the reservoir layer having a thickness of 10 to 100 μm and comprising a first adhesive composition comprising:
         (A) a (meth)acrylic acid alkyl ester-based adhesive;
         (B) a polyvinyl acetate-based adhesive, wherein said polyvinyl acetate-based adhesive has a weight average molecular weight range of from 150,000 to 1,000,000;
         (C) a plasticizing component; and
         (D) isosorbide dinitrate;
      the first adhesive composition satisfying the following conditions (I) through (III):
         (I) the weight of (A) to the weight of (B) is from 60:40 to 10:90;
         (II) the weight ratio of (C) based on the weight of the first adhesive composition is 20 to 40%; and
         (III) the weight ratio of (D) based on the weight of the first adhesive composition is 22 to 45%,
      and the adhering releasing layer having a thickness of 3 to 25 μm and comprising a second adhesive composition, the second adhesive composition comprising components (A), (B), (C), and (D) as defined above and satisfying the following conditions (I') through (III'):
         (I') the weight of (A) to the weight of (B) is from 0:100 to 100:0;

(II') the weight ratio of (C) based on the weight of the second adhesive composition is 0 to 40%; and (III') the weight ratio of (D) based on the weight of the second adhesive composition is 0 to 30%, and (2) laminating the adhesive layer to the flexible support, wherein the flexible support comprises a fabric having 5 to 60 g/m² unit area weight.

18. The method of claim 17, wherein the conditions (I) through (III) satisfied by the first adhesive composition are:

(I) the weight of (A) to the weight of (B) is from 60:40 to 10:90;

(II) the weight ratio of (C) based on the weight of the first adhesive composition is 20 to 40%; and (III) the weight ratio of (D) based on the weight of the first adhesive composition is 25 to 35%, and the conditions (I') through (III') satisfied by the second adhesive composition are:

(I') the weight of (A) to the weight of (B) is from 0:100 to 100:0;

(II') the weight ratio of (C) based on the weight of the second adhesive composition is 0 to 40%; and (III') the weight ratio of (D) based on the weight of the second adhesive composition is 10 to 30%.

19. The method of claim 17, wherein the conditions (I) through (III) satisfied by the first adhesive composition are:

(I) the weight of (A) to the weight of (B) is from 60:40 to 10:90;

(II) the weight ratio of (C) based on the weight of the first adhesive composition is 25 to 40%; and (III) the weight ratio of (D) based on the weight of the first adhesive composition is 28 to 35%.

20. The method of claim 17, wherein the reservoir layer has a thickness of from 30 to 80 μm and the conditions (I) through (III) satisfied by the first adhesive composition are:

(I) the weight of (A) to the weight of (B) is from 60:40 to 10:90;

(II) the weight ratio of (C) based on the weight of the first adhesive composition is 30 to 40%; and (III) the weight ratio of (D) based on the weight of the first adhesive composition is 28 to 35%, and the thickness of the adhering releasing layer is from 7 to 20 μm and the conditions (I') through (III') satisfied by the second adhesive composition are:

(I') the weight of (A) to the weight of (B) is from 60:40 to 10:90;

(II') the weight ratio of (C) based on the weight of the second adhesive composition is 30 to 40%; and (III') the weight ratio of (D) based on the weight of the second adhesive composition is 10 to 30%, provided that the concentration of (D) is higher in the reservoir layer than in the adhering releasing layer.

21. The method of claim 17, further comprising the following step (3):

(3) applying a heat treatment or a reduced pressure treatment to the isosorbide dinitrate-containing patch to reduce the water content of the patch to 0.5 wt % or less.

22. The method of claim 17, wherein the conditions (I') through (III') satisfied by the second adhesive composition are:

(I') the weight of (A) to the weight of (B) is from 60:40 to 10:90;

(II') the weight ratio of (C) based on the weight of the second adhesive composition is 30 to 40%; and (III') the weight ratio of (D) based on the weight of the second adhesive composition is 0 to 10%, and the method further comprises the following step (3):

(3) moving the isosorbide dinitrate from the reservoir layer to the adhering releasing layer by heating the adhesive layer comprising the reservoir layer and the adhering releasing layer at a temperature of from 40° C. to 100° C.

23. The method of claim 22, wherein the isosorbide dinitrate is moved from the reservoir layer to the adhering releasing layer by heating the adhesive layer comprising the reservoir layer and the adhering releasing layer at a temperature of from 40° C. to 60° C. for from 8 hours to 48 hours.

24. The method of claim 22, wherein the isosorbide dinitrate is moved from the reservoir layer to the adhering releasing layer by heating the adhesive layer comprising the reservoir layer and the adhering releasing layer at a temperature of from 40° C. to 45° C. for from 20 hours to 168 hours.

25. A method for manufacturing an isosorbide dinitrate-containing patch, comprising:

(1) forming an adhesive layer comprising an adhesive composition comprising:

(A) a (meth)acrylic acid alkyl ester-based adhesive;

(B) a polyvinyl acetate-based adhesive, wherein said polyvinyl acetate-based adhesive has a weight average molecular weight range of from 150,000 to 1,000,000;

(C) a plasticizing component; and (D) isosorbide dinitrate, the adhesive composition satisfying the following conditions (I) through (III):

(I) the weight of (A) to the weight of (B) is from 50:50 to 10:90;

(II) the weight ratio of (C) based on the weight of the adhesive composition is 25% to 57%; and (III) the weight ratio of (D) based on the weight of the adhesive composition is 0% to 10%, (2) laminating the adhesive layer to a flexible support, wherein the flexible support comprises a fabric having 8 to 30 g/m² unit area weight, (3) impregnating a laminate of the adhesive layer and the flexible support with a solution of isosorbide dinitrate (D), and (4) applying a heat treatment or a reduced pressure treatment to the isosorbide dinitrate-containing patch to reduce the water content of the patch to 0.5 wt % or less.

26. The method of claim 25, wherein the adhesive layer comprises one or more layers.

* * * * *